(12) United States Patent
Overholser et al.

(10) Patent No.: US 8,309,161 B2
(45) Date of Patent: Nov. 13, 2012

(54) ALUMINUM OXIDE COATED IMPLANTS AND COMPONENTS

(75) Inventors: Ronald Overholser, Columbia City, IN (US); Bryan Smith, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 12/208,842

(22) Filed: Sep. 11, 2008

(65) Prior Publication Data

US 2009/0012624 A1    Jan. 8, 2009

Related U.S. Application Data

(63) Continuation of application No. 11/240,716, filed on Sep. 30, 2005, now abandoned.

(51) Int. Cl.
*A61F 2/36* (2006.01)
*A61F 2/34* (2006.01)
*A61F 2/32* (2006.01)
*A61F 2/02* (2006.01)
*B05D 3/02* (2006.01)
*C23C 14/08* (2006.01)

(52) U.S. Cl. ...... 427/2.1; 427/2.24; 427/2.25; 427/2.26; 427/248.1; 623/11.11; 623/20.14; 623/22.21; 623/20.35

(58) Field of Classification Search ........... 427/2.24, 427/2.26, 2.27, 526, 528, 2.1–2.31
See application file for complete search history.

(56) References Cited

U.S. PATENT DOCUMENTS

| | | | |
|---|---|---|---|
| 4,016,606 A | | 4/1977 | Murray et al. |
| 4,404,045 A | | 9/1983 | Thevenot et al. |
| 4,474,849 A | * | 10/1984 | Fujimori et al. ............ 428/332 |
| 4,637,837 A | | 1/1987 | Von Matuschka et al. |
| 4,673,408 A | * | 6/1987 | Grobbelaar ............. 623/20.29 |
| 4,743,308 A | | 5/1988 | Sioshansi et al. |
| 5,037,438 A | | 8/1991 | Davidson |
| 5,123,924 A | | 6/1992 | Sioshansi et al. |
| 5,308,412 A | | 5/1994 | Shetty et al. |
| 5,516,588 A | * | 5/1996 | van den Berg et al. ....... 428/469 |
| 5,855,950 A | * | 1/1999 | Bunker ................ 427/2.27 |
| 6,210,726 B1 | | 4/2001 | Schiller et al. |
| 6,261,322 B1 | | 7/2001 | Despres, III et al. |
| 7,169,485 B2 | * | 1/2007 | Kohara et al. ............. 428/701 |
| 7,776,393 B2 | * | 8/2010 | Tamagaki et al. ......... 427/248.1 |
| 2003/0008764 A1 | | 1/2003 | Wang et al. |
| 2003/0035894 A1 | | 2/2003 | Derflinger et al. |
| 2005/0079200 A1 | | 4/2005 | Rathenow et al. |
| 2005/0191408 A1 | * | 9/2005 | Aharonov et al. ........... 427/2.27 |
| 2005/0276990 A1 | * | 12/2005 | Kohara et al. ............... 428/469 |

FOREIGN PATENT DOCUMENTS

| | | |
|---|---|---|
| CN | 1278307 A | 12/2000 |
| DE | 44 22 686 A1 | 1/1996 |
| EP | 0 248 117 A2 | 12/1987 |
| EP | 937786 A2 * | 8/1999 |
| EP | 1 616 978 A | 1/2006 |
| JP | 08-126695 A | 5/1996 |
| WO | WO 92/17623 A | 10/1992 |
| WO | WO 99/24634 A1 | 5/1999 |

OTHER PUBLICATIONS

Cloud et al. TEM investigation of alpha alumina films deposited at low temperature. Surface and Coatings Technology vol. 203, Issues 5-7, Dec. 25, 2008, pp. 808-811.*
Zywitzki et al. Effect of substrate temeprature on teh structure and properties of Al2O3 layers reactively deposited by pulsed magnetron sputtering. Surface and Coatings Technology, Col. 82, 1996, pp. 169-175.*
Jin et al. Localized epitaxial growth of alpha-AI2)3 thin films on Cr2O3 template by sputter deposition at low substrate temperature. Applied Physics Letters 82, 1024-1026. Feb. 17, 2003.*
Armin et al., *Alternative Bearing Surfaces in Total Joint Replacement, ASTM STP 1346*: 197-209 (1998).
Bunker et al., *J. Am. Ceram. Soc.*, 76(2): 347-349 (Feb. 1993).
Clarke et al., *Clin. Orthop. Relat. Res.*, 379: 34-40 (Oct. 2000).
Davidson, *Proceedings of the Satellite Symposium 3 on Ceramics in Substitutive and Reconstructive Surgery of the 7th CIMTEC-World Ceramics Congress*: 157-166 (Jun. 27-30, 1990).
Filiaggi et al., *J. Biomed. Mater. Res.*, 33(4): 225-238 (1996).
Fisher et al, *48th Annual Meeting of the Orthopaedic Research Society*, Paper No. 0102 (Feb. 2002).
Good et al., *J. Bone Joint Surg.*, 85-A (Suppl. 4): 105-110 (2003).
Heinke, "Structural Characteristics of Metals and Ceramics" in *Metal and Ceramic Biomaterials* (Ducheyne et al., eds.), vol. 1, Chapter 2, pp. 39-43 (CRC Press, Inc., 1984).
Kelly et al. , *J. Vac. Sci. Technol. A*, 17(3): 945-953 (May/Jun. 1999).
Minoda et al., *50th Annual Meeting of the Orthopaedic Research Society*, Poster No. 1501 (Mar. 2004).
Muratoglu et al., *50th Annual Meeting of the Orthopaedic Research Society*, Paper No. 0297 (Mar. 2004).
Prengel et al., *Surface and Coatings Technology*, 68-69: 217-220 (1994).
Rieu, *Clin. Mater.*, 12: 227-235 (1993).
Ruiz et al., *J. Biomed. Mater. Res.*, 46(2): 179-185 (Aug. 1999).

(Continued)

Primary Examiner — Timothy Meeks
Assistant Examiner — Cachet I Sellman
(74) *Attorney, Agent, or Firm* — Barnes & Thornburg LLP

(57) ABSTRACT

The invention provides a medical implant device or component thereof comprising a metal substrate, an intermediate coating, and an outer coating of aluminum oxide, as well as a method of making such a medical implant device or component thereof.

9 Claims, No Drawings

OTHER PUBLICATIONS

Schneider et al., *J. Vac. Sci. Technol. A*, 15(3): 1084-1088 (May/Jun. 1997).
Seino et al., *J. Vac. Sci. Technol. A*, 20(3): 634-637 (May/Jun. 2002).
Silva et al., "Biomaterial-Tissue Interfaces" in *Advances in Biomaterials*, 10: 363-376 (Elsevier Science Publishers B.V.A, 1992).
Toni et al., *J. Arthroplasty*, 9(4): 435-444 (Aug. 1994).
Urban et al., *J. Bone Joint Surg.*, 83-A(11): 1688-1694 (Nov. 2001).
Widding et al., *48th Annual Meeting of the Orthopaedic Research Society*, Poster No. 1009 (Feb. 2002).
Yen et al., *Biomaterials*, 22(2): 125-133 (2001).
Yen et al., *J. Biomed. Mater. Res.*, 54(3): 412-418 (Mar. 2001).
Zywitzki et al., *Surface and Coatings Technology*, 86-87: 640-647 (1996).
Zywitzki et al., *Surface and Coatings Technology*, 94-95: 303-308 (1997).
*European Patent Office*, Search Report in European Patent Application No. 06255364.9 (Mar. 8, 2007).
Watchel et al., "Tribology of alumina and diamond-like coatings for orthopaedic applications," Surface Modification Technologies V, Proceedings of the fifth international conference held in Birmingham, UK, Sep. 2-4, 1991, The Institute of Materials, 1992, 15 pages.
Maruyama, "Effect of low-friction ion-treated femoral heads on polyethylene wear rates" CORR 370: 183-91, 2000.
Kamali "The Influence of RGCA Tin Coating on Reduction of UHMWPE Wear in Knee Prostheses" 50th ORS: 1481, 2004.
Pappas, "Titanium nitride ceramic film against polyethylene. A 48 million cycle wear test." CORR 317: 64-70, 1995.
Jindal et al. "Adhesion measurements of chemically vapor deposited and physically vapor deposited hard coatings on WC—Co substrates" Thin Solid Films 154: 361-375, 1987.
Vidakis et al. "The VDI 3198 indentation test evaluation of a reliable qualitative control for layered compounds" Journal of Materials Processing Technologies 143-144: 481-485, 2003.
Laurent, Trans. 27th Soc. For Biomaterials: 543, 2001.
Cataldo, "Boride surface treatments" Advanced Matls & Processes, pp. 35-38, Apr. 2000.
Toni et al. "Bone demineralization induced by cementless aiurnina-coated femoral stems" Arthroplasty, 9:4, pp. 435-444, 1994.
Steinmann et al. "Adhesion Testing by the Scratch Test Method: the Influence of Intrinsic and Extrinsic Parameters on the Critical Load" Thin Solid Films 154: 333-349, 1987.
Knotek, et al. "Surface layers on cobalt base alloys by boron diffusion" Thin Solid Films 45: 331-339, 1977.
Taylor "A study of the ageing behaviour of a cobalt based implant alloy" J. Mater. Sci. 18: 3265-3280, 1983.
Kilner, "Static mechanical properties of cast and sinter-annealed cobalt-chromium surgical implants" J. Mater. Sci. 21: 1349-1356, 1986.
Dobbs, "Heat treatment of cast Co-Cr-Mo for orthopaedic implant use" J. Mater. Sci. 18: 391-401, 1983.
Onate, "Wear reduction effect on ultra-high-molecular-weight polyethylene by application of hard coatings and ion implantation on cobalt chromium alloy, as measured in a knee wear simulation machine" Surf. Coatings Tech 142-144: 1056-1062, 2001.
Chinese First Office Action, Chinese Patent Application No. 200610143296.8, Aug. 31, 2011, 3 pages.

\* cited by examiner

ALUMINUM OXIDE COATED IMPLANTS AND COMPONENTS

CROSS-REFERENCE TO A RELATED APPLICATION

This application is a continuation of co-pending U.S. patent application Ser. No. 11/240,716, filed Sep. 30, 2005, the disclosure of which is incorporated by reference.

FIELD OF THE INVENTION

This invention pertains to medical implant devices and components thereof, as well as methods of making medical implant devices and components thereof.

BACKGROUND OF THE INVENTION

Interest in medical prosthetic implants with longer lifespans has increased due to demographic shifts in the population of medical implant recipients. As in the general population, the life expectancy of medical implant recipients has been steadily increasing. Additionally, the number of younger and more active implant recipients has also been increasing. Each of these trends highlights the importance of longer-lasting, high performance orthopedic implants that are less likely to require replacement, i.e., revision, during a recipient's lifetime.

Thus, of concern is that such longer-lasting implants be able to withstand years of wear and the variety of stresses associated with being implanted in a body. Joint replacement implants must be strong enough to tolerate changing mechanical loads, while at the same time, transferring portions of the loads to surrounding bone tissue. Another requirement is that the bearing (i.e., articulating) surfaces of joint replacement implants must be resistant to a corrosive environment and withstand body and surface contact forces and adhesive and abrasive wear processes that are associated with movement of the joint. Mechanical and physical properties suitable for withstanding years of mechanical loading and wear can be difficult to find in a single material.

Currently, metals, including metal alloys, are used as structural material for medical implants. Metal alloys such as steel, cobalt alloys, and titanium alloys exhibit a range of strengths, hardness, and fatigue resistance. Moreover, these metals can be formed by metalworking processes and machined. Commonly, implants include a metal bearing surface configured to move against a second bearing surface composed of a low-friction polymer, such as ultra high molecular weight polyethylene (UMWHPE), or another metal component. Particles and debris have been known to dissociate from these implants due to wear processes once implanted in a recipient's body. These dissociated particles are problematic, as those that become disposed in surrounding tissue have been linked to inflammation and degradation of surrounding tissue. This inflammatory reaction can lead to joint pain and loosening of the implant. Eventually, the condition can require removal and replacement of the implant in a complicated and troublesome revision procedure. Hard particles such as cement particles (in devices implanted with cement) or delaminated metal from an implant's porous or textured fixation surface can become lodged in the articulating surface of a polymeric implant or trapped between opposing articulating surfaces and scratch the previously smooth metallic surface, and thereby reduce implant performance, increase abrasive wear of the articulating counterface, and even lead to delamination of other surface material.

Previous efforts to reduce the wear of metallic implant surfaces have included surface modifications such as ion implantation, gas nitriding, and high temperature oxidation. Each approach can have limitations. For example, generally, the peak hardness of surfaces obtained by ion implantation and nitriding is not as high as the peak hardness that can be obtained by other surface modifications such as ceramic overlay coatings. Ion implantation approaches can also have theoretical or economic limits on the depth of the surface modified material. Substrates underlying surface layers created by high temperature oxidation (e.g., Zr-2.5 Nb alloy) are not as strong or hard as other substrate metals (e.g., CoCrMo or Titanium alloys) and may not be compatible with conventional processes for creating porous tissue ingrowth surface structures.

In a different approach, bulk metal substrates in implants have been replaced with bulk ceramics, such as in certain hip implants that include bulk oxide ceramic femoral heads. Such ceramics do not corrode in the body, are wear-resistant, and they can withstand large compressive loads. However, bulk ceramics tend to be stiffer and more brittle than metals. Reports have shown that some bulk ceramic implant components are prone to catastrophic fracture and, thus, may require immediate revision.

To obtain the beneficial wear properties of bulk ceramics without the risk of fracture, there have been attempts to apply ceramic coatings to the articulating surface of a metal implant. The properties of these ceramic coatings are quite varied, depending on the ceramic type and manner of application. However, the development of implants coated with particular ceramics (e.g., aluminum oxide) has been limited. Techniques for applying particular ceramic coatings have resulted in coatings that are alternately too thin, porous, unstable in the body, or poorly adhered to the underlying metal substrate for use on orthopaedic bearing surfaces.

BRIEF SUMMARY OF THE INVENTION

The invention provides a medical implant device or component thereof that includes a metal substrate other than steel, an intermediate coating other than aluminum oxide, and an outer coating of aluminum oxide. In particular, the invention provides a medical implant or implant component comprising a substrate of a metal other than steel, an intermediate coating of a material other than aluminum oxide adhered to the substrate surface, and an outer coating of aluminum oxide adhered to at least a portion of intermediate coating, desirably by having been deposited by physical vapor deposition onto at least a portion of the intermediate coating.

The invention also provides a method of making a medical implant device or component thereof. The method includes (a) providing a medical implant device or component thereof that comprises a metal substrate other than steel, (b) applying an intermediate coating of a material other than aluminum oxide to the substrate surface, and (c) depositing an outer coating of aluminum oxide by physical vapor deposition onto at least a portion of the intermediate coating.

DETAILED DESCRIPTION OF THE INVENTION

The invention provides a medical implant device or component thereof that includes a metal substrate, an intermediate coating, and an outer surface coating of aluminum oxide.

The medical implant device or component thereof can be any suitable medical implant device or component thereof. Suitable medical implant devices and components thereof include, but not limited to, orthopedic prostheses for the hip, knee, ankle, shoulder, elbow, and spine. Exemplary medical implant devices include a full or partial knee arthroplasty prosthesis, full or partial hip arthroplasty prosthesis, full or partial elbow arthroplasty prosthesis, full or partial wrist arthroplasty prosthesis, full or partial shoulder arthroplasty prosthesis, full or partial ankle arthroplasty prosthesis, and full or partial articulating spinal segment arthroplasty prosthesis. Exemplary components of medical implant devices include a femoral component (e.g., for replacing one or more femoral condyles) or a tibial component (e.g., for replacing at least a portion of a proximal tibial plateau) of a knee prosthesis (e.g., a uni-compartmental or total knee arthroplasty prosthesis), a femoral component (e.g., for replacing at least the proximal portion or head of the femur) or an acetabular cup (e.g., for replacing the hip bone's femoral socket) of a hip prosthesis, a humeral component (e.g., for replacing the distal portion of the humerus) or an ulnar component (e.g., for replacing the proximal portion of the ulna) of an elbow prosthesis, a metacarpal component (for replacing at least a portion of one or more metacarpal bones) or radial component (for replacing the distal portion of the radius) of a wrist prosthesis, a humeral component (e.g., for replacing the proximal portion or head of the humerus) or glenoid component (e.g., for replacing the glenoid or socket portion of the scapula) of a shoulder prosthesis, a tibial component (e.g., for replacing the distal portion of the tibia) or talar component (e.g., for replacing the proximal portion of the talus) of an ankle prosthesis, and an endplate component (e.g., for contacting the superior or inferior portion of a cervical, lumbar or thoracic vertebra) or spacer component (e.g. for insertion between endplate components) of a vertebral disc prosthesis.

The metal substrate can be any suitable metal substrate other than steel. Unless otherwise indicated herein, the term "metal" refers to pure metals and metal alloys. The "metal substrate" can be the entire, or nearly the entire, structure that substantially forms the medical implant device or component thereof; or the "metal substrate" can be a portion of the structure that substantially forms the medical implant device or component thereof, with the remainder of the structure that substantially forms the medical implant device or component thereof comprising other material. When the metal substrate is a portion of the structure that substantially forms the medical implant device or component thereof, the metal substrate can be the entire surface of, or a portion of the surface of, the structure that substantially forms the medical implant device or component thereof.

While the metal substrate can be any suitable portion of the medical implant device or component thereof, the metal substrate desirably includes a bearing surface. As used herein, a "bearing surface" refers to a portion of the medical implant device or component thereof that is configured to articulate with or move against a second surface when the medical implant device or component thereof is implanted in the body of a patient. The second surface can be bone, cartilage, or other material that is native to the body. More commonly, the second surface is another, i.e., a second, bearing surface in a medical implant device or component thereof. For example, in certain embodiments of the invention, a coated bearing surface (comprising a substrate, an intermediate coating, and an outer coating of aluminum oxide) is designed to bear against a second bearing surface of the same or different medical implant device or component thereof, wherein the second bearing surface can comprise any suitable material, e.g., metal, ceramic, polymer, or combinations thereof. Typically, the second bearing surface comprises a polymer such as an ultra high molecular weight polyethylene (UHMWPE), which is widely used as a polymeric bearing surface, e.g., in knee implants and hip implants. The second bearing surface may also comprise another coated bearing surface or an uncoated metallic bearing surface.

Exemplary bearing surfaces include (a) the surface at the distal end of a femoral component of a knee prosthesis, which surface articulates with a second bearing surface on the tibial component of the prosthesis, (b) the surface of a femoral head component of a hip prosthesis, which surface articulates against the second bearing surface of the acetabular cup component of the prosthesis, (c) an articulating surface of an elbow arthroplasty prosthesis, e.g., the surface of the distal end of the humoral component or the surface of the proximal end of the ulnar component, which surfaces articulate against each other, (d) the surface of a humoral head component of a shoulder prosthesis, which surface articulates against the glenoid component of the prosthesis, (e) the surface of a talus component of an ankle prosthesis, which surface articulates against the tibial component of the arthroplasty, and (f) the surface of a spinal disc replacement prosthesis' endplate component, which surface articulates against another endplate or the core/spacer component disposed between two endplates of the prosthesis.

The metal substrate can comprise, consist essentially of, or consist of any suitable metal, desirably a biocompatible metal. Desirable metals include metals with suitable mechanical properties for use in joint replacement prostheses. The metal preferably does not readily corrode in a patient into which the medical implant device or component thereof is intended to be placed, and preferably possesses appropriate strength and fatigue characteristics. Exemplary preferred metal substrates include cobalt, cobalt alloys, titanium, titanium alloys, and mixtures of these. Suitable cobalt-chromium alloys include, but are not limited to, the cast, forged, and wrought cobalt-28-chromium-6-molybdenum (Co28Cr6Mo) alloys described in, for example, ASTM Standards F75-01, F799-02, and F1537-00, respectively. Suitable titanium-aluminum alloys include, but are not limited to, the titanium-3-aluminum-2.5-vanadium alloy (Ti-3Al-2.5V) described in, for example, ASTM Standard F2146-01 and the titanium-6-aluminum-4-vanadium (Ti-6Al-4V) alloy described in, for example, ASTM Standard F136-02a. ASTM standards are available in print or electronic media from ASTM International (West Conshohocken, Pa.).

An intermediate coating of a material other than aluminum oxide is adhered to the metal substrate. The intermediate coating can comprise, consist essentially of, or consist of any suitable material or combination of materials. Exemplary intermediate coatings include titanium aluminum nitride (TiAlN), chromium aluminum nitride (CrAlN), aluminum nitride (AlN), titanium carbonitride (TiCN), titanium nitride (TiN), titanium aluminide (TiAl), chromium oxide ($Cr_2O_3$), chromium nitride (CrN), and combinations thereof. The material of the intermediate coating preferably has one or more physical or chemical properties (e.g. a thermal expansion coefficient, elastic modulus, crystal structures, and/or chemical compatibility) intermediate between the physical or chemical properties of the metal substrate and the outer coating of aluminum oxide, so as to provide a transition gradient of those properties on the surface of the medical implant device or component thereof. Through this transition gradient of mechanical and physical properties, the intermediate coating can provide a desirable level of adhesion between the metal substrate and the outer coating of aluminum oxide.

The intermediate coating can be of any suitable thickness. The intermediate coating desirably has a thickness of about 0.001 µm, e.g., about or 0.01 µm or more, 0.05 µm or more, about 0.1 µm or more, or about 0.2 µm, or about 0.4 µm or more. The intermediate coating desirably has a thickness of about 10 μm or less, e.g., about 5 μm or less, about 2 μm or less, or about 1 μm or less.

The intermediate coating is adhered to the metal substrate by any suitable technique including physical vapor deposition (PVD), chemical vapor deposition (CVD), and thermal spraying deposition (e.g., plasma spraying). Generally, PVD is preferred because of its ability to produce high quality, dense coatings of many metals and ceramic compounds.

The intermediate coating can constitute one or more layers, which can be separately applied by any suitable technique and adhered to each other. Each layer desirably comprises the material(s) described herein for the intermediate coating and is applied by the techniques described herein for the intermediate coating.

One or more of the following considerations desirably is taken into account when selecting the material and thickness of the intermediate coating. The material and thickness of the intermediate coating preferably promotes the adherence of the outer coating of aluminum oxide to the metal substrate. Thus, the material and thickness of the outer coating desirably improve the indirect adherence of the outer coating to the metal substrate relative to the adherence of the outer coating directly to the same substrate (i.e., without the intermediate coating). Common methods for assessing the adhesion of ceramic coatings on metals include scratch and indentation tests. Suitable tests are described in, e.g., Steinmann et al., Thin Solid Films 154:333-349 (1987), Jindal et al., Thin Solid Films 154:361-375 (1987), Vidakis et al., Journal of Materials Processing Technologies 143-144:481-485 (2003), and the German standard VDI 3198. Desirably, the material and thickness of the intermediate coating provides one or more physical or chemical properties (e.g. a thermal expansion coefficient, elastic modulus, crystal structures, and/or chemical compatibility) intermediate between the physical or chemical properties of the metal substrate and the outer coating of aluminum oxide, so as to provide a transition gradient of those properties on the surface of the medical implant device or component thereof. Also desirably, the material and thickness of the intermediate coating increase the outer coating's resistance to wear and shear stress (relative to the outer coating's resistance without the intermediate coating) during production and/or after implantation in a body of a patient.

A coating of aluminum oxide (also known as $Al_2O_3$ or alumina) is adhered onto at least a portion of the intermediate coating. The outer coating is so named because it is outermost on the medical implant device or component thereof relative to the metal substrate and the intermediate coating disposed between the metal substrate and the outer coating. The aluminum oxide can be any suitable aluminum oxide. Desirably, the aluminum oxide is in a biocompatible and thermodynamically-stable α-phase, having a crystalline structure with hexagonal close-packing oxygen atoms and aluminum atoms occupying two thirds of the octahedral lattice interstices. The outer coating preferably includes a layer of single phase α-aluminum oxide. The α phase is distinguished from the metastable κ-phase and γ-phase aluminum oxides. These less stable forms of aluminum oxide are reportedly more likely to solubilize when disposed in a body of a patient. See, e.g., Toni et al., J. Arthroplasty, 9: 4 (1994).

The outer coating can be of any suitable thickness. The outer coating desirably has a thickness of about 1 μm or more, e.g., about 1.5 μm or more, about 2 μm or more, about 2.5 μm or more, about 3 μm or more, about 3.5 μm or more, or about 4 μm or more, or about 5 μm or more. In general, the upper limit of the thickness of the outer coating is determined by considerations that can, but do not necessarily, include production cost, coating adhesion, residual stresses, scratch and indentation resistance, and substrate fatigue resistance and coating fatigue resistance. The outer coating typically has a thickness of about 100 μm or less, about 50 μm or less, about 40 μm or less, about 30 μm or less, about 20 μm or less, or about 10 μm or less. The outer coating desirably has a thickness of about 15 μm or less, e.g., about 12 μm or less, about 10 μm or less, or about 9 μm or less, or about 8 μm or less.

The outer coating is disposed on, and adhered to, the intermediate coating by physical vapor deposition (PVD) onto at least a portion of the intermediate coating. PVD techniques include ion plating, arc discharge evaporation, activated reactive evaporation (ARE), and magnetron sputtering techniques. PVD aluminum oxide films have been deposited by reactive evaporation and reactive sputtering of a metallic aluminum target in an oxygen environment and direct sputtering of an oxide target. Preferred PVD techniques include ionized magnetron sputtering, pulsed magnetron sputtering, RF magnetron sputtering and AC magnetron sputtering. As used herein, PVD techniques do not include ion beam assisted deposition (IBAD). PVD equipment and services are available commercially, e.g., from Teer Coatings, Ltd (Droitwich, Worcestershire, England) and Balzers A G, Principality of Liechtenstein. Moreover, PVD techniques are described in Seino et al., J. Vac. Sci. Tech., A20: 634-637 (2002), Kelly et al., J. Vac. Sci. Tech., A17: 945-953 (2002), Zywitzki et al., Surface & Coatings Tech., 94-95: 303-308 (1997), Zywitzki et al., Surface & Coatings Tech., 86-87: 640-647 (1996), and U.S. Pat. No. 6,210,726.

PVD typically can be used at relatively low temperatures. Although the formation of the stable α phase aluminum oxide coating requires heating of the substrate to be coated, the required temperatures are typically less than with thermal CVD, where α phase aluminum oxide coatings are formed above 1000° C. (Prengel et al., Surf. Coat. Tech., 68-69:217 (1994)). Thus, for example, a stable a phase aluminum oxide coating can be applied by PVD using temperatures of less than about 1000° C., e.g., less than about 950° C., less than about 900° C., or less than about 850° C. Using PVD, an α phase aluminum oxide coating can be applied at temperature ranges between about 500° C. and about 850° C., e.g., between about 700° C. and about 800° C., between about 600° C. and about 700° C., or between about 500° C. and 600° C. Reduced temperatures used for PVD also allow optimization of the mechanical properties of the coating/substrate system.

PVD can be used to produce very fine-grained aluminum oxide coatings with fine surface finishes that are advantageous for bearing applications. The bearing surfaces of medical implant devices or components thereof often need to be polished to minimize friction between bearing surfaces and the wear rates of a bearing couple. A fine grained aluminum oxide coating that requires less or no post-coating polishing can be advantageous, as imperfect polishing can cause surface defects in the coating microstructure and contribute to non-uniform coating thicknesses on an implant, both of which could reduced performance.

The invention also provides a method for making the medical implant device or component thereof of the invention. The method of comprises (i) providing a medical implant device or component thereof that comprises a metal substrate other than steel, the substrate comprising a surface, (ii) applying an intermediate coating of a material other than aluminum oxide to the substrate surface, and (iii) depositing an outer coating of aluminum oxide by physical vapor deposition onto at least a portion of the intermediate coating. The various elements of the method are as previously described in the context of the medical implant device or component thereof of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of making a medical implant device or component thereof, the method comprising:
   (i) providing a medical implant device or component thereof that comprises a metal substrate other than steel, the substrate comprising a surface,
   (ii) applying an intermediate coating of a material other than aluminum oxide to the substrate surface, the intermediate coating having a thickness of 1 μm to 10 μm, and
   (iii) depositing an outer coating of α-aluminum oxide by physical vapor deposition at a temperature between 500° C. and 600° C. onto at least a portion of the intermediate coating.

2. The method of claim 1, wherein the metal substrate comprises a biocompatible metal or metal alloy selected from the group consisting of cobalt, cobalt alloys, titanium, titanium alloys, and mixtures thereof.

3. The method of claim 1, wherein the metal substrate comprises cobalt chromium alloy or a titanium alloy.

4. The method of claim 1, wherein the metal substrate comprises Co-28Cr-6Mo, Ti-3Al-2.5V, or Ti-6Al-4V.

5. The method of claim 1, wherein the intermediate coating includes a material selected from the group consisting of titanium aluminum nitride (TiAlN), chromium aluminum nitride (CrAlN), aluminum nitride (AlN), titanium carbonitride (TiCN), titanium nitride (TiN), chromium oxide (Cr2O3), titanium aluminide (TiAl), chromium nitride (CrN), and combinations thereof.

6. The method of claim 1, wherein the device is a prosthetic device for use in a hip joint, knee joint, elbow joint, shoulder joint, ankle joint, or an articulating vertebral segment.

7. The method of claim 1, wherein
the device is a (i) knee or (ii) hip replacement prosthesis that comprises a femoral portion,
the femoral portion comprises a bearing surface for contacting (i) a tibial proximal articular surface or (ii) an acetabular cup, and
at least a portion of the bearing surface is the substrate surface.

8. The method of claim 7, wherein
the metal substrate comprises Co-28Cr-6Mo, Ti-3Al-2.5V, or Ti-6Al-4V, and
the intermediate coating includes a material selected from the group consisting of titanium aluminum nitride (TiAlN), chromium aluminum nitride (CrAlN), aluminum nitride (AlN), titanium carbonitride (TiCN), titanium nitride (TiN), chromium oxide ($Cr_2O_3$), titanium aluminide (TiAl), and combinations thereof.

9. The method of claim 1, wherein
the outer coating comprises aluminum oxide that is at least 1 μm thick, and
adherence of the outer coating to the substrate surface is improved by the intermediate coating relative to without the intermediate coating.

* * * * *